(12) United States Patent
Oberthür et al.

(10) Patent No.: US 6,369,042 B1
(45) Date of Patent: Apr. 9, 2002

(54) ANTIOXIDATIVE VITAMIN $B_6$ ANALOGS

(76) Inventors: Walter Oberthür, Astertrasse 9, D-85402 Kransberg; Andreas J. Kesel, Chammunsterstrasse 47, D-81827 Munich, both of (DE)

(*) Notice: Subject to any disclaimer, the term of this patent is extended or adjusted under 35 U.S.C. 154(b) by 0 days.

(21) Appl. No.: 09/437,627

(22) Filed: Nov. 10, 1999

Related U.S. Application Data

(63) Continuation-in-part of application No. PCT/EP99/02960, filed on Apr. 30, 1999.
(51) Int. Cl.[7] .................. A61K 31/70; A61K 31/675; C07H 1/00; C07D 211/72
(52) U.S. Cl. ........................ 514/54; 514/23; 514/89; 514/92; 536/4.1; 536/18.7; 536/123; 546/301
(58) Field of Search ............... 546/301; 536/4.1, 536/13.7, 123, 18.7; 514/13, 89, 92, 54, 23

(56) References Cited

FOREIGN PATENT DOCUMENTS

WO    WO 98/20013    5/1998

OTHER PUBLICATIONS

Kesel et al., Interconvertible (Z/E)–Stereoisomers of a Vitamin B6 Coenzyme Analog Derived from Pyroidoxal 5'–Phosphate and Rhodanine, *Tetrahedron* 52(47):14787–14800 (1996).

Kesel et al. A New Antioxidative Vitamin B6 Analogue Modulates Pathophysiological Cell Proliferation and Damage, *Bioorg. & Med. Chem.* 7:359–367 (1999).

*Primary Examiner*—Elli Peselev
(74) *Attorney, Agent, or Firm*—Heller Ehrman White & McAuliffe LLP

(57) ABSTRACT

The present invention relates to novel antioxidative Vitamin $B_6$ analogs and their use in the cosmetic, dermatological, pharmaceutical and/or nutritional fields. Analogs can be provided in suitable formulations intended in particular for caring for the skin, make up for the skin, protection from the sun of the skin, as well as for the treatment of diseases of the skin and bone, and viral, parasitic and fungal infections.

9 Claims, 5 Drawing Sheets

ANTIOXIDATIVE VITAMIN $B_6$ ANALOGS

RELATED APPLICATIONS

This application is a CIP of PCT/EP99/02960 filed Apr. 30, 1999.

FIELD OF THE INVENTION

The present invention relates to novel antioxidative Vitamin $B_6$ analogs and their use in the cosmetic, dermatological, pharmaceutical and/or nutritional fields.

BACKGROUND

Skin is subject to insults by many extrinsic and intrinsic factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin. Whether extrinsic or intrinsic, these factors result in visible signs of skin aging and environmental damage, such as wrinkling and other forms of roughness (including increased pore size, flaking and skin lines), and other histological changes associated with skin aging or damage.

In recent years, intrinsic factors contributing to the premature aging of skin have been investigated. Substances having anti-oxidizing activity, those having an activity of scavenging reactive oxygen species or radicals, or an activity of inhibiting the generation of reactive oxygen species in the presence of a metal ion (Fenton reaction) have attracted attention, because reactive oxygen species or radicals are responsible for a variety of diseases as well as the aging of skin such as hardening, development of wrinkles and pigmentation, and the generation of reactive oxygen species in the presence of metal ion causes the oxidative disorders in the body which are responsible for a variety of diseases and the aging of skin described above.

Additionally, free radicals also have been associated with the development of tumors. It is believed that free radicals damage DNA and change the normal cells into potential tumor cells.

One effort to reduce the signs of aging that has received attention in recent years is the use of alpha-hydroxy acids (AHAs). Products with AHAs are marketed for a variety of purposes: to smooth fine lines and surface wrinkles, to improve skin texture and tone, to unblock and cleanse pores, to improve oily skin or acne, and to improve skin condition in general. Cosmetics that contain AHAs have become widely used in recent years despite many unanswered questions about their safety. Recently, a study sponsored by the cosmetics industry indicates that these products may make users more sensitive to sunlight and especially to the ultraviolet (UV) radiation component of sunlight. UV exposure can damage the skin and at high doses, especially over a long period, can cause skin cancer. Thus, it would be advantageous, for example, for cosmetics containing alpha-hydroxy acids to contain a UV protectant.

Patient compliance refers to the extent to which actual behaviour of a patient coincides with medical advice. Approximately two-thirds of patients do not follow their doctor's advice. Some of the reasons for not taking the medication as prescribed are complexity of drug regimen, embarrassment, e.g., children who need to take medications at school, and forgetfulness. Thus, an easy method of treatment of diseases would be desirable.

Thus, it would be desirable to have a compound that is easily applied or administered which would provide (1) benefit to the skin, (2) treatment of diseases, (3) an advantageous means of drug/vitamin delivery and/or (4) cosmotological enhancements.

SUMMARY OF THE INVENTION

The invention concerns new vitamin $B_6$ analogs with antioxidative, radical-scavenging functions which counteract pathophysiological disorders especially connected with aging processes. The new agents counteract against oxidation- and age-mediated, acquired and inherited disease-related pathophysiological disorders. These functions render the new analogs useful for the treatment of these disorders which include but are not limited to multiple sclerosis, degenerative cell, tissue and organ processes, gerontological diseases such as Alzheimer's disease, Diabetes Type I, allergies, neurological disorders, skin diseases such as psoriasis, bone and bone tissue disorders such as osteoporosis. The new analogs are also antidotes against organo-phosphorous compounds.

The new compounds are also suitable for the treatment of disorders associated with defects of the vitamin $B_6$ metabolism and therefore act as vitamin $B_6$ antagonists.

The analogs of this invention have important anti-infective potential, for example antiviral activity, antiparasitic activity, and antifungal activity. Especially useful are the analogs of the invention for the treatment of viral diseases caused by enveloped viruses such as hepatitis, herpes and retro viruses but are also useful for the treatment of other viral infections, such as infection from influenza or rhinovirus.

The new agents have cytoprotecting, immunomodulating, stimulating and inhibiting activity in vitro, suppress cell proliferation in cancer cells and cause cell death in these cells.

These functions enable the new compounds to be useful for cosmetic or cosmeceutical or nutritional applications, keratological or skin-caring applications such as skin protection and skin restoration, in improving health, fitness, hygiene of the human and animal body, skin, teeth, oral gums, nails, lips and hair. The new analogs are also useful agents for the treatment and prevention of sun or skin burns. In addition, the new analogs may be used as protecting dyes. The new analogs are also useful agents for the release of vitamins. They aid in the transport of pharmaceutical, cosmeceutical and cosmetic agents into cells, in particular specialized cells. As the new analogs are dephosphorylated by endogenous phosphorylases they will be transported into the cells where they are rephosphorylated and unable to pass out of the cell in phosphorylated form.

Toxic or cytopathic effects have not been observed with the analogs of this invention in a number of cell culture systems. It appears that the new analogs act as relatively untoxic polyspecific drugs with an amphoteric structure, as multiplex buffer molecules.

The new analogs have the general formula (Formula I)

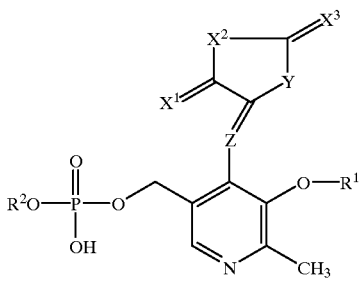

wherein $R^1$ is hydrogen, or acyl with 2–22 carbons (excluding retinoyl);

$R^2$ is hydrogen, or aryl with 6–30 carbons; provided that at least one of $R^1$ or $R^2$ is not hydrogen;

$X^1$, $X^2$ and $X^3$ are independently O, S, or $NR^3$;

$R^3$ is hydrogen, alkyl with 1–6 carbons, or acyl with 2–6 carbons;

Y is O, S, or NH;

Z is CH or N;

and include salts and common esters derived from unreacted remaining functional groups in Formula I. In a preferred embodiment $X^1$ is O, $X^2$ is NH, $X^3$ is S, Z is CH and Y is S.

The salts and common esters selected do not in a substantial way adversely affect the therapeutic, cosmetic, hygiene, anti-aging, cosmeceutical and nutritional functions of the new analogs.

Analogs in which $R^1$ is an α-hydroxy acid such as glycolic or lactic or malic acid residue and their common salts and esters are preferred. Also preferred are analogs in which $R^1$ is derived from an FDA approved or accepted agent such as carminic acid and their common salts and esters. Carninic acid is a coloring agent approved by the FDA in foods and drugs. Also preferred are analogs in which $R^1$ is derived from an FDA approved or accepted agent, a vitamin such as pantothenic acid which analogs may function as Vitamin $B_3$ or $B_5$ delivering agents or ascorbic acid (Vitamin C) and their common salts and esters. Also preferred are analogs in which $R^1$ is derived from glucuronic acid or a glucuronic acid derivative such as hyaluronic acid with a molecular weight of $5 \times 10^4$ to $8 \times 10^6$ and their common salts and esters.

More preferred is a subgroup of analogs in which $R^1$ has the above meanings and $R^2$ is hydrogen and their common salts and esters.

Most preferred in this subgroup are analogs in which Z is CH, $X^1$ is oxygen, $X^2$ is NH, $X^3$ and Y are S, and their salts and common esters which do not in a substantial way adversely affect the therapeutic, cosmetic, hygiene, anti-aging, cosmeceutical and nutritional functions of the compounds in the subgroup.

Analogs in which $R^2$ is derived from a phenolic hydroxy group containing derivative such as phenol are preferred and their common salts and esters. Also preferred are analogs in which $R^2$ is derived from phenolic hydroxy group containing derivative such as α-tocopherol and their common salts and esters. Also preferred are analogs in which $R^2$ is derived from a coenzyme such as ubiquinone and their common salts and esters.

More preferred is a subgroup of analogs in which $R^2$ has the above meanings and $R^1$ is hydrogen and their common salts and esters. Most preferred in this subgroup are analogs in which Z is CH, $X^1$ is oxygen, $X^2$ is NH, $X^3$ and Y are S and their salts and common esters which do not in a substantial way adversely affect the therapeutic, cosmetic, hygiene, anti-aging, cosmeceutical and nutritional functions of the compounds in the subgroup.

The analogs radical-scavenging function reduces the concentration of radicals nitrogen-containing radicals such as nitric oxide, their epigones (peroxinitrite S-nitrosothiols), the hydroxyl radical, the superoxide anion radical, singlett oxygen; they act as nitric oxide synthetase inhibitor and thus display general anticancer activity where the cancer is caused or believed to be caused by cancerogenic radicals. Therefore, the analogs of this invention act as antileukemic, anti-breast cancer, anti-skin cancer active compounds. The analogs also display immunologic activity and act as cytokine/trophokine modifiers, as anti-psoriatic or anti-allergic reagents.

The analogs of the invention also act as-a skin and/or tissue compatible coloring agent whose color can be influenced and modified by a number of factors such as degree of hydratization or derivativization (different salts exhibit different colors and the free acids also display different colors), the addition of other pigments, choice of the pH, or solvents. Color modification can be introduced with the appropriate choice of the cation. For example, for the analogs in which $R^1$ is derived from carminic acid the magnesium, calcium, aluminum or other cations permit to vary the color from yellow to red to violet. Colored lacquers may be obtained, also varnishes for lipsticks, hair, nail coloring and other cosmetic uses (as additives to Mascara, or as Kajal additive). A number of analogs are fluorescent in a suitable environment. For example, the analogs in which $R^1$ is derived from carminic acid display fluorescence emission at 575 mm. This can be used for hair coloring in clubs, discos and for show business. The colored hair fluoresces through light emission when illuminated in night clubs or by UV illumination, but the coloring agent protects from UV-introduced radical-mediated damages of hair or skin.

The new analogs are useful as ultra-radical scavengers and skin-protectors. In this respect, the analogs in which $R^1$ is derived from α-tocopherol is particularly useful as ultra-radical scavenger and also protects and stabilizes cosmetic cremes, lotions, essences or fluids. Therefore, the analogs of this invention are useful as multi-purpose stabilizers for many dermatological products (in ointments, creams, lotions, fluids, essences, special drug delivery systems such as sustained delivery systems for therapeutic, cosmetic or nutritional applications).

As radical-scavengers the new analogs also function as flexible skin-caring agents, protect against the influence of ultraviolet light, in particular in areas where there is an ozone deficiency. With these functions the new analogs are useful to prevent premature skin aging, modulate environmental stress and preserve humidity, and act as a humectant.

The new analogs act as wound-healing promoters and improve infection resistance.

The analogs in which $R^2$ is derived from ubiquinone augment the respiratory activity of ubiquinone $Q_{10}$ by modulating mitochondrial apoptosis. This results in preserving energy and enhances the rejuvenation process.

The analogs in which $R^1$ is derived from glucuronic acid derivatives such as hyaluronic acid act as anti-oxidative skin protectors, as tissue clarifying agents, revitalize skin moisture by combining Vitamin $B_6$ with hyaluronic acid. Their radical-scavenging and radiation protecting properties vitalize the human skin against environmental noxae, skin

DETAILED DESCRIPTION

Figure 1:
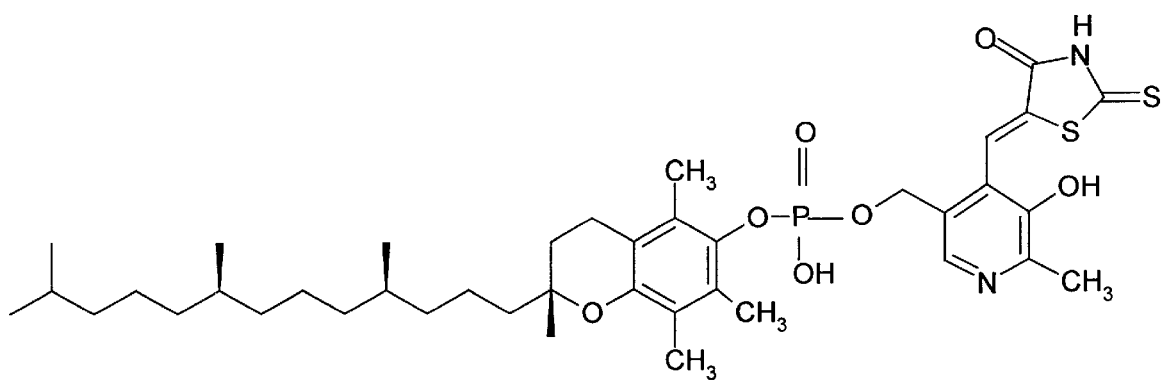
FIG. 1 is the c-tocopherol derivative.
Figure 2:
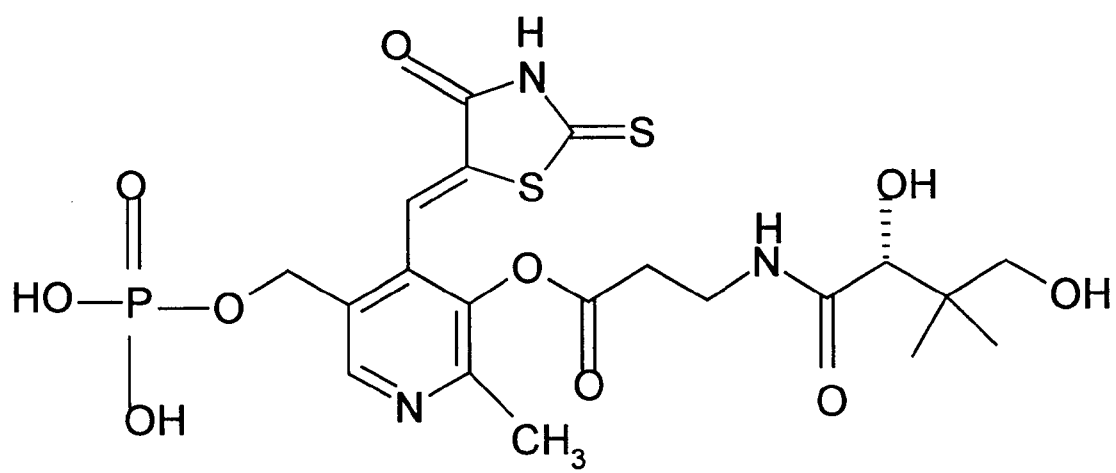
FIG. 2 is the pantothenic acid derivative.
Figure 3:
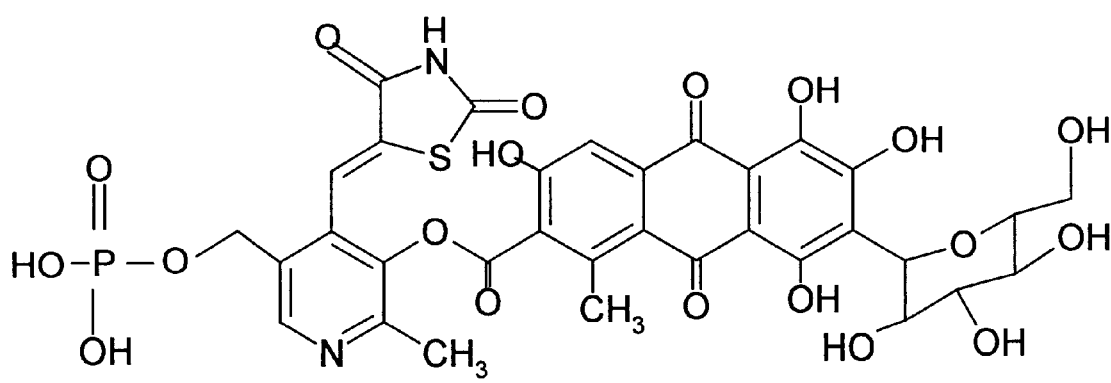
FIG. 3 is the carminic acid derivative.
Figure 4:
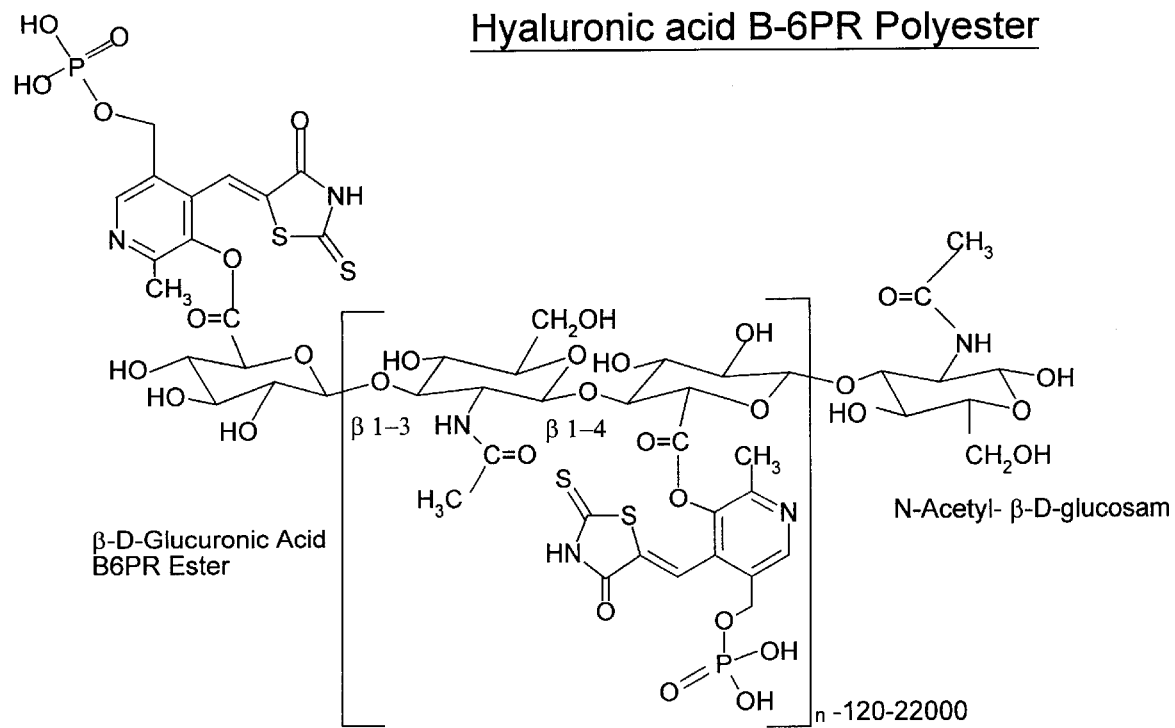
FIG. 4 is the hyaluronic acid derivative.
Figure 5:
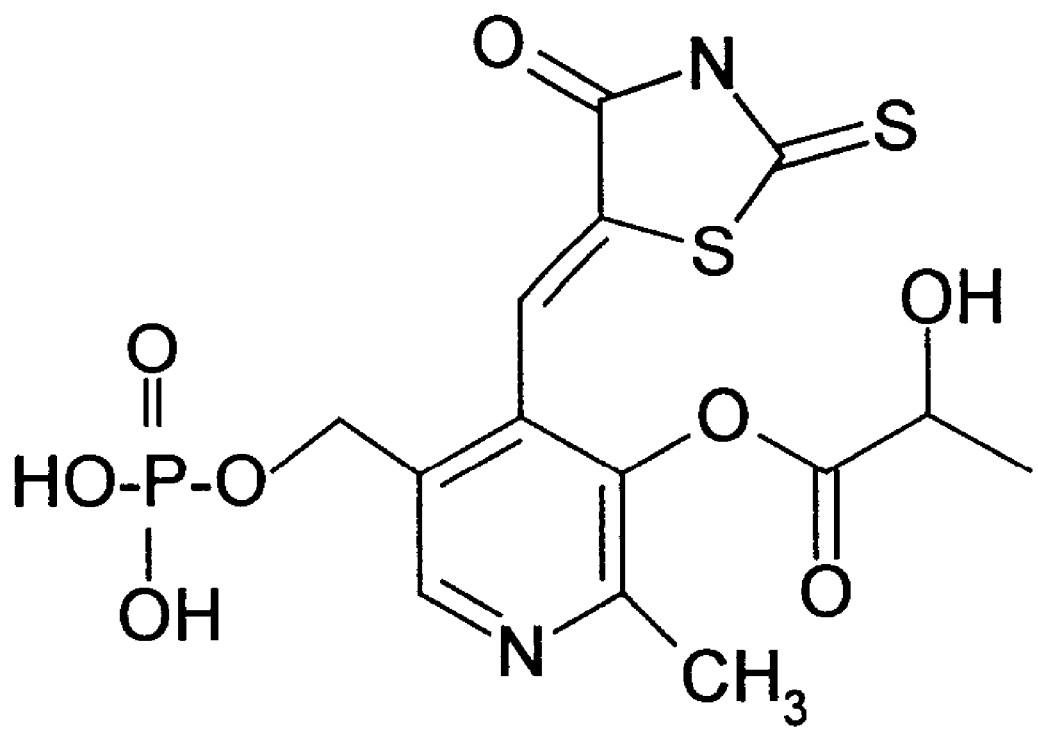
FIG. 5 is the lactic acid derivative.

The inventive compounds described herein are useful for a number of diseases, conditions and uses. Their use is dictated by the active biomolecule that is condensed with the compound of Formula II or III. While any number of biomolecules, and in particular those biomolecules approved by the FDA, may be condensed to yield the inventive vitamin B6 analogs, preferred embodiments are described herein. Thus, these embodiments are meant to be illustrative and not limiting in any way.

The term "aryl" refers to a monovalent organic radical derived from an aromatic hydrocarbon typically with 5 to 21 carbon atoms, preferably 6 to 16 carbon atoms, having a single ring (e.g., phenyl), or two or more condensed rings, preferably 2 to 3 condensed rings (e.g., naphthyl), or two or more aromatic rings, preferably 2 to 3 aromatic rings, which are linked by a single bond (e.g. biphenyl). The aryl radical may optionally be mono-, di- or tri-substituted, independently, with branched or straight chain alkyl, cycloalkyl with 3 to 12 carbon atoms, branched or straight chain alkoxy, cycloalkoxy with 3 to 12 carbon atoms, hydroxy, fluoro, chloro, bromo, trifluoromethyl, cyano, nitro and/or difluoromethoxy, etc.

The term "alkyl" refers to a branched or straight chain monovalent alkyl radical of one to twenty-four carbon atoms and may be optionally substituted with an oxo, alkoxy, hydroxy or halogen. The alkyl chain may be interrupted with either S, O or NH. This term is further exemplified by such radicals as methyl, ethyl, n-propyl, isopropyl, i-butyl, n-butyl, t-butyl, pentyl, n-hexyl, n-heptyl, etc.

The term "cycloalkyl" refers to a cyclic monovalent alkyl radical of three to nine carbon atoms. This term is further exemplified by such radicals as cyclopropyl, cyclopentyl, cyclohexyl or cycloheptyl.

The term "alkoxy" refers to the group —O—R' where R' is alkyl of 1–6 carbon atoms.

Preparation of the Compounds

The new analogs can be prepared by procedures known in the art. The analogs in which $R^1$ is acyl with 2–22 carbons may be prepared by reacting an acid chloride of the formula I with an alkali salt of a compound of the formula (Formula II)

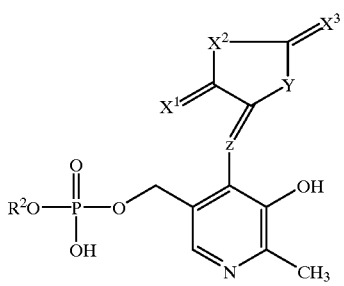

wherein the substituents have the same meaning as described above for the compounds of Formula I.

The reaction is carried out under substantially water-free conditions at temperatures between 0 and 30° C. For example, the compound of Formula II may be reacted with lactic acid chloride or carminic acid derivatives. Specifically, (Z)-5-[[5-hydroxy-6-methyl-3-[(phosphonooxy)methyl]-4-pyridinyl]methylene]-2-thiooxo-4-thiazolidinone monosodium chloride may be reacted with protected lactic acid or carminic acid derivatives to afford the new analogs of the following formulae (Formula I/1 and I/2):

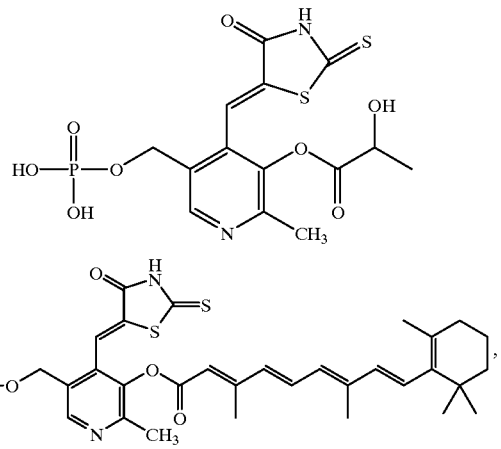

Similarly, a compound of Formula II, a derivative or a salt thereof, may be reacted with a protected glucuronic acid derivative, pantothenic acid or a derivative thereof, protected hyaluronic acid or a derivative thereof or another acyl group with 2–22 carbons to afford the corresponding analog of Formula I.

Alternatively, the new analogs may be prepared by reacting a compound of Formula II with a condensing agent such as a carbodiimide, for example dialkyl or dicycloalkyl, especially 1,3-dicyclohexyl carbodiimides or salts of such carbodiimides may be used as coupling agents. Other carbodiimides may also be used such as N,N'-carbonyldiimidazole. These coupling agents usually act as dehydrating agents which would remove water to form as condensation products the new analogs.

In general, when carrying out a process of this invention, those amino, hydroxy or carboxylic or other reactive groups which are not to participate in the esterification or condensation reaction must be protected until (1) either de-protection yields the final product; or (2) a specific protected group is to be involved in the next synthetic step or in a series of steps; or (3) the presence of the unprotected group in the ensuing reaction steps leading to the final product would not modify the intended sequence of reactions.

The analogs in which R² is aryl with 6–30 carbons may be prepared by reacting a compound of Formula III

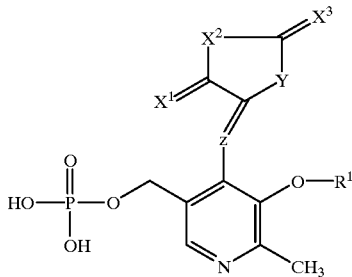

with a condensing agent such as a carbodiimide, for example dialkyl or dicycloalkyl, especially 1,3-dicyclohexyl carboiimides or salts of such carbodiimides may be used as coupling agents. The substituents in Formula III have the same meanings as described above for the compounds of Formula I. Other carbodiimides may also be used such as N,N'-carbonyldiimidazole. These coupling agents usually act as dehydrating agents which would remove water t form the as condensation products the new analogs.

In general, when carrying out a process of this invention, those amino, hydroxy or carboxylic or other reactive groups which are not to participate in the esterification or condensation reaction must be protected until (1) either de-protection yields the final product; or (2) a specific protected group is to be involved in the next synthetic step or in a series of steps; or (3) the presence of the unprotected group in the ensuing reaction steps leading to the final product would not modify the intended sequence of reactions.

"Protecting group" is a chemical group that (a) preserves a reactive group from participating in an undesired chemical reaction; and (b) can be easily removed after protection of the reactive group is no longer required; and (c) does not modify the desired course of steps to the final product.

"Amino-protecting group" is a protecting group that preserves a reactive amino group that otherwise would be modified by certain chemical reactions. It includes lower alkanoyl groups with 2–6 carbons such as the acetyl, propionyl or trifluoroacetyl, the allyloxycarbonyl or the "FMOC" group or other groups derived from halocarbonates such as benzylchlorocarbonate, the trityl or substituted trityl groups, or the phthalyl group.

"Hydroxy-protecting group" is a group that protects the hydroxy group. Suitable hydroxy-protecting groups include ether-forming groups that can be easily removed after completion of all required reaction steps, such as the optionally substituted benzyl or trityl group, the tetrahydropyranyl, silyl, trialkyl silyl ether groups and the allyl groups. These protecting groups can be removed under conventional de-protecting conditions.

A "carboxylic acid—protecting group" is usually an ester of the free carboxylic acid group that can be easily removed after protection is no longer required, for example by hydrogenolysis.

The above-described condensation reactions with carbodiimides are usually carried out in absolute basic solvents such as pyridine at 0–30° C., preferably room temperature for an extended time period, preferably from 12–200 hours, most preferably 24–120 hours. An acidic ion exchange matrix such as DOWEX® may be used as catalyst.

Tocopherol

Vitamin E is a powerful vitamin and antioxidant, circulating in the blood and detoxifying free radicals (destructive by-products-of metabolism), prevents damage to cell membranes, thereby reducing the risk of heart disease and cancer. Further, vitamin E keeps "bad" cholesterol (LDL) from turning into even worse cholesterol—oxidized LDL—which initiates buildup of arterial plaque (atherogenesis) and can lead, ultimately, to serious heart disease. Finally, it also speeds healing in burn and post-operative patients and, recent studies suggest, seems to ease the pain and swelling of osteoarthritis and rheumatoid arthritis, to reduce the risk of cataracts, to bolster the immune system, even to slow the progress of Parkinson's disease.

A fat-soluble vitamin, vitamin E exists in the form of tocopherols and tocotrienols. Four different tocopherols have been identified, and although the most active is alpha-tocopherol, researchers now believe there's a symbiotic relationship among the different tocopherols, that all work in concert to promote good health. The unit of measurement for vitamin E is the D-alpha-tocopherol equivalent, abbreviated as alpha-TE and computed in milligrams.

Most common Vitamin E formulas contain from 3 to 15 mg. of E. The current RDA for Vitamin E is 10 mg per day for men, 8 mg per day for women,. 3 mg alpha-TE per day for neonates and 4 mg alpha-TE per day for infants. Pregnant and lactating women should increase their Vitamin E intake to approximately 10–12 mg per day.

Vitamin B5

Pantothenic acids' most important function is as an essential component in the production of coenzyme A, a vital catalyst that is required for the conversion of carbohydrates, fats, and protein into energy. Pantothenic acid is also referred to as an antistress vitamin due to its vital role in the formation of various adrenal hormones, steroids, and cortisone, as well as contributing to the production of important brain neuro-transmitters such as acetylcholine. In addition to helping to fight depression pantothenic acid also supports the normal functioning of the gastrointestinal tract and is required for the production of cholesterol, bile, vitamin D, red blood cells, and antibodies.

Most common B-complex formulas contain from 10 to 100 mg. of B5, though daily doses up to 1000 mg are not uncommon, especially for treatment of arthritis and allergies. The current RDA for pantothenic acid is 10 mg.

Ascorbic Acid (Vitamin C)

Ascorbic acid is essential for many oxidation reactions in the body. For instance, oxidation of tyrosine and phenylalanine requires an adequate supply of ascorbic acid, and ascorbic acid plays a role in formation of hydroxyproline, an integral constituent of collagen, which in turn is essential for growth of subcutaneous tissue, cartilage, and bone.

Physiologically, the major function of ascorbic acid appears to be maintenance of normal intercellular substances throughout the body. This includes the formation of collagen, probably because of the action of ascorbic acid in synthesis of hydroxyproline. It also enhances the intercellular cement substance between the cells, the formation of bone matrix, and the formation of tooth dentin.

Deficiency of ascorbic acid result in the failure of wounds to heal. This is caused by failure of the cells to deposit collagen fibrils and intercellular cement substances. As a result, healing of a wound may require several months instead of the several days ordinarily necessary. Failure to deposit collagen fibrils and other intercellular cement substances lead to blood vessel walls to become extremely fragile. The capillaries are especially likely to rupture and many small petechial hemorrages occur throught the body.

Lack of ascorbic acid causes cessation of bone growth. The cells of the growing epiphyses continue to proliferate but no new matrix is laid down and the bones fracture easily. When ossified bone fractures the osteoblasts fail to lay down new matrix and the fracture fails to heal.

Lactic Acid

Lactic acid is an alpha-hydroxy acid used as a moisturizer, pH adjuster and exfoliant in cosmetics. It is sometimes referred to as 2-hydroxypropanoic acid. Alpha-Hydroxy Acid molecules thin the stratum corneum (the skin's scaly outer layer), as well as hasten cell turnover which makes skin more resilient. These acids help to dissolve the bond, or "glue", that holds dead cells on the surface of the skin, help repair the aging cellular level (because the molecules are small enough to penetrate the deeper layers of the skin). This helps in firming the underlying tissues for greater elasticity as well as encouraging more tissue activity. Alpha-Hydroxy acids help with age spots, lines, wrinkles, sun damage, tighten pores as well as help correct both dry and oily skin problems. Cosmetics that contain alpha hydroxy acids (AHAs) have become widely used in recent years. AHA products cause exfoliation, or shedding of the surface skin. The extent of exfoliation depends on the type and concentration of the AHA, its pH (acidity), and other ingredients in the product. Most cosmetics sold to consumers contain AHAs at levels up to 10 percent. Though found mainly in face and body creams and lotions, AHAs also can be used in other cosmetics, such as shampoos and cuticle softeners.

Carminic Acid

A major cause of skin cancer is repeated sunburns to the skin. Damage to DNA due to ultra violet radiation, excited forms of oxygen, and free radicals can cause mutations which lead to carcinogenesis. Carminic acid conjugates protect from UV-radiation induced radical-mediated damage.

Hyaluronic Acid

Hyaluronic acid (HA) is a naturally occurring glycosaminoglycan. It is a constituent of the intercellular matrix of connective tissue that exists in almost all vertebrates. HA is found at high concentrations in the umbilical cord, in the aqueous and vitreous humor of the eye, in synovial fluid in joints, in group A and C hemolytic streptococci, and in rooster combs.

In nature, HA usually exists as a sodium salt (sodium hyaluronate) forming a highly viscous fluid with exceptional lubricating qualities. It plays an important role in a number of physiological functions, including protection and lubrication of cells, maintenance of the structural integrity of tissues, transport of molecules and cells, and fluid retention and regulation.

USES OF THE INVENTIVE COMPOUNDS

The inventive compounds find a number of uses depending on the biomolecule conjugated with the compound of Formula II or III. The inventive compounds have uses in the personal care field as skin moisturizers, sunscreens, shampoos, facial cleansers, and the like. Similarly, the products that are useful for such human uses may also be used on animals to help eliminate most problem skin conditions. For example, fungus, scaling, hot spots, dry skin or itching caused by flea bites or lice may be eliminated upon application of the inventive compound.

The inventive compounds also find use in the cosmetic field as lipstick, hair color skin dyes and the like. In the preferred cosmetics area, the compositions of the invention can be used in such products as antiperspirants; bath and shower soaps, granules, bars, oils or gels; after-bath creams and lotions; shampoo and conditioners; makeup including base or foundation, blush, rouge, eye liner, eye shadow, mascara, and lip gloss; lip moisturizers and lip ointment; message creams and lotions; sun screen, sun tanning and skin bleaching compositions; skin paint; wrinkle remover; cold creams, cleansing creams, emollient creams and hand creams; perfume and fragrances; hair waving, bleaching, setting products, rinses and dressings; insect repellents, preshave and after-shave lotions and creams, shave creams, depilatories and the like. The products can be in the form of creams, lotions, liquids, powders, pastes, and the like, as would be appreciated by one of ordinary skill in the art.

The hair cosmetic compositions according to the present invention embrace all the cosmetic compositions applied to hair, for example, pre-shampoo treatment agent, shampoo, hair rinse, hair conditioner, hair treatment, setting lotion, blow styling lotion, hair spray, foam styling agent, gel styling agent, hair liquid, hair tonic, hair cream, hair growth accelerator, hair nourishment, 1st component for permanent wave, 2nd component for permanent wave, permanent hair dye and temporary hair dye. Skin dye compositions employing the products of this invention are generally less concentrated than those used as hair colorants. Typically, they will contain from about 0.01% to 10%, preferably 0.05% to 1% of at least one product of the invention dissolved, emulsified or suspended in a pharmaceutically acceptable skin vehicle which may be aqueous or non-aqueous and may comprise water, inert oils, emollients, surfactants, buffers or other additives such as those illustrated in the examples. The inventive compounds that fluoresce will find use in a theatrical setting as well as by nightclub patrons.

The inventive compounds find use in skin diseases such as psoriasis, glossitis, neurodermitis and the like, as well as bone and cartilage diseases such as osteoporosis. Furthermore, topical application may function as a UV protectant.

The inventive compounds also find use in the pharmaceutical field as a vitamin therapy or supplement, in the treatment of infective diseases, for example, viral, parasitic, bacterial and fungal diseases. Especially preferred is the use for the treatment of viral infections, in particular of such viral infections which are caused by enveloped viruses like hepanaviruses, herpesviruses or retroviruses, e.g. HIV. Also contemplated are viruses such as influenza or papillomaviruses. Furthermore, the compounds according to the invention are also suitable for the fighting of tumor diseases, for example, leukemias, especially T cell leukemias, or of skin tumors like malignant melanoma or Kaposi's Sarcoma. Surprisingly, they show a selective cytotoxic action against malignant cells, not against normal cells.

Personal Care Products

Personal care products can be in the form of powders, pressed powders, sprays, creams, foams, aerosols, lotions, gels, ointments, and liposomal and other suitable formulations. Items contemplated herein include body powders, lotions, gels, aqueous compositions and solutions, nail polishes, make-up, body paints, shaving cream, shampoo and the like. As described herein, the novel analogs are applied to the skin, hair, lips, nails or other suitable body locations by way of the inventive compositions and are fluorescent under blacklight (UV) illumination found in nightclubs and the like.

The compositions of the present invention are useful for regulating mammalian skin condition (especially human skin, more especially human facial skin), including visible and/or tactile discontinuities in skin, signs of skin aging, and visible and/or tactile discontinuities in skin associated with skin aging (including fine lines, wrinkles, large pores, surface roughness and other texture discontinuities associated with aged skin). Such regulation includes prophylactic and therapeutic regulation.

Regulating skin condition involves topically applying to the skin a safe and effective amount of a composition of the present invention. The amount of the composition which is applied, the frequency of application and the period of use will vary widely depending upon the level of the inventive compound(s) and/or other components of a given composition and the level of regulation desired, e.g., in light of the level of skin aging present in the subject and the rate of further skin aging.

UV Protectant

Energy from the sun reaches the earth as visible, infrared, and ultraviolet rays. Ultraviolet A is made up of wavelengths 320 to 400 nanometers (nm) in length; ultraviolet B wavelengths are 280 to 320 nm; and ultra- violet C wavelengths are 100 to 280 nm. Because the earth's atmosphere absorbs the UVC wavelengths, the only ultraviolet rays that reach the earth's surface are UVA and UVB. While a small amount of exposure to sunlight can be healthy and pleasurable, too much can be dangerous. Exposure to UV rays is linked to a number of harmful health effects.

Skin cancer and other skin damage. Some effects of sunlight on the skin are visible within hours or days (e.g., sunburn and tanning); other effects are delayed and cumulative and may be seen in months to years (e.g., skin cancer and photoaging). Skin cancer. The incidence of skin cancer cases is increasing rapidly. Over 1,000,000 new cases of skin cancer are likely to be diagnosed in the U.S. this year. Eighty percent of the UV exposure occurs before the age of 18 and the damage is cumulative over time. UV radiation exposure is implicated in the formation of non-melanoma and melanoma cancers.

Premature aging. Sun exposure also causes premature aging of the skin. Photoaging of the skin is different than normal chronological aging. Regular sun bathers show photoaging changes early in life (before 30 years of age); while chronologically aged skin shows changes later (after 40 or more years of age). Freckling, fine wrinkling, and dilatation of capillaries are often seen early in the photoaging process; later on the photoaged skin develops irregular pigmentation, often called liver spots. Both photoaging and chronological aging cause wrinkling and loss of skin elasticity; however, they occur much earlier when the skin has been overexposed to the sun.

Nail Polishes and Lacquers

In another embodiment the inventive compounds are incorporated into a nail polish or nail enamel. In this embodiment the inventive compounds are mixed with a modified cellulose ester as the major film former, copolymerizable monomer, modifying resin, plasticizer, photoinitiator,and solvents.

Typical copolymerizable monomers are (meth)acrylic acid, crotonic acid, maleic acid, fumaric, itaconic acid and their anhydrides, cyanoacrylic; esters of (meth)-acrylic acid such as allyl, methyl, ethyl, n-propyl, isopropyl, butyl, tetrahydrofurfuryl, cyclohexyl, isobormyl, n-hexyl, n-octyl, isooctyl, 2-ethylhexyl, lauryl, stearyl, benzyl, and substituted phenoxyl, behenyl; di(meth)acrylate esters of ethylene and propylene glycols, 1,3-butylene glycol, 1,4-butanediol, diethylene and dipropylene glycols, triethylene and tripropylene glycols, 1,6-hexanediol, neopentyl glycol, polyethylene glycol, and polypropylene glycol, ethoxylated bisphenol A, propoxylated neopentyl glycol; tri(meth)acrylate esters of tris-(2-hydroxyethyl)isocyanurate, trimethylolpropane, pentaerythritol, glycerol, ethoxylated and propoxylated glycerol; tetra(meth)acrylate esters of pentaerythritol; acrylonitrile, vinyl acetate, vinyl toluene, styrene, N-vinylpyrrolidinone, and alpha-methylstyrene.

Typical modifying resins include homopolymers and copolymers of (meth)acrylic acid; alkyl esters of (meth) acrylic acid such as allyl, methyl, ethyl, n-propyl, isopropyl, butyl, tetrahydrofurfuryl, cyclo-hexyl, isobomyl, n-hexyl, n-octyl, isooctyl, 2-ethyl-hexyl, lauryl, stearyl, benzyl; (meth)acrylated urethane, epoxy, and polyester resins, silicone acrylates.

Typical solvents include lower molecular weight alcohols such as ethanol, propanol, isopropyl alcohol, butanol, pentanol, hexanol, and 2-ethylhexanol; glycols such as ethylene and propylene glycols; ketones such as acetone, 2-butanone, and 2-pentanone; esters such as methyl and ethyl acetate, isopropyl acetate, butyl and isobutyl acetate, ethylene glycol diacetate, propylene glycol diacetate.

Typical plasticizers include alkyl esters of phthalic acid such as dimethyl phthalate, diethyl phthalate, dipropyl phthalate, dubutyl phthalate, and dioctyl phthalate; citrate esters such as triethyl citrate and tributyl citrate; triacetin and tripropionin; and glycerol monoesters.

Typical photoinitiators include benzoin and benzoin ethers, benzilketals, alpha, alpha-dialkoxyacetophenone derivatives, alpha-hydroxyalkylphenones, and mixtures of benzophenone and tertiary amines.

Cosmetic Formulations

In general, most cosmetic and pharmaceutical creams and lotions contain oils, waxes, lanolins, sterols, humectants, emollients, thickening agents, proteins, preservatives, emulsifiers, silicones and the like as would be appreciated by one of ordinary skill in the art.

Bath Powders

Numerous bath powders exemplified herein, are suitable for use in combination with the inventive compounds described herein. Such bath powders are preferably non-detergent with a pH close to neutral. In addition, capsular delivery vehicles, such as liposomes or time release delivery vehicles, preferably microcapsules, that contain the inventive compounds, and that are pH, temperature sensitive, or that dissolve in water or that are otherwise released are preferred for use herein. Upon contact with the warm water or with water of a particular pH the contents of the capsule or pellet will be released, preferably over time.

Suitable bath powders and bubble baths and other bubble compositions for use in these combinations are well known to those of skill in the art [see, e.g., U.S. Pat. Nos.: 5,478,501; 4,565,647; 5,478,490; 5,412,118; 5,401,773; and many other examples]. These may be modified by adding the inventive compounds disclosed herein.

Dust or Powder

Another embodiment of the compounds described herein is as a dust or powder substance, or a vapor, such as for use in the theatrical productions. In this embodiment, lyophilized or desiccated forms, micronized powdered forms, or, a suitable composition, of the inventive compounds are encapsulated in readily rupturable or time release or temperature or pH or light sensitive microspheres or capsules, as described above. Preferable encapsulating agents are light or temperature sensitive so that upon exposure to the environment, the contents are released from the capsules. Moisture or oxygen in the air or a spray of water on the skin in the vicinity of the "dust" will allow the dust to adhere to the skin. The dust can be added to another powder, such as body powder.

Lotions, Gels and Other Topical Application Formulations

For application to the skin, the macro or microparticles of the inventive compounds may be added to cosmetic compositions. The compositions may be provided in the form of gels, creams, lotions, solids, and other compositions, such as solutions and suspensions, aerosols or solid base or vehicle known in the art to be non-toxic and dermatologically acceptable to which sufficient number of such particles are added under conditions in which the contents are released into the gels, creams, lotions, solids, solutions or suspensions, or aerosols. Upon application to the skin the gels, creams, lotions, solids, solutions or suspensions, or aerosols may provide a method of administering the inventive compounds directly to the affected area or transdermal administration if systemic therapy is desired.

(1) Lotions

The lotions contain an effective concentration of the inventive compounds. Preferably, the reagents are encapsulated in a vehicle that releases its contents upon exposure to light or temperature, such that as the contents of the vehicle are released they provide a continuous administration of the inventive compounds. The effective concentration is that sufficient to produce the desired effect, e.g., hydration, UV protection, compound delivery and the like, when contacting the skin. Any emollients known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.
(b) Silicone oils, including dimethylpolysiloxanes, methylphenylpolysiloxanes, water-soluble and alcohol-soluble silicone-glycol copolymers.
(c) Triglyceride fats and oils, including those derived from vegetable, animal and marine sources. Examples include but are not limited to, castor oil, safflower oil, cotton seed oil, corn oil, olive oil, cod liver oil, almond oil, avocado oil, palm oil, sesame oil, and soybean oil.
(d) Acetoglyceride esters, such as acetylated monoglycerides.
(e) Ethoxylated glycerides, such as ethoxylated glyceryl monstearate.
(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
(g) Alkenyl esters of fatty acids having 10 to 20 carbon atoms. Examples thereof include, but are not limited to, oleyl myristate, oleyl stearate, and oleyl oleate.
(h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids.
(i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols.
(j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof
(k) Ether-esters, such as fatty acid esters of ethoxylated fatty alcohols.
(l) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.
(m) Polyhydric alcohols and polyether derivatives, including, but not limited to, propylene glycol, dipropylene glycol, polypropylene glycol [M.W. 2000–4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200–6000], methoxy polyethylene glycols 350, 550, 750, 2000, 5000, poly(ethylene oxide) homopolymers [M.W. 100,000–5,000,000], polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), C15–C18 vicinal glycol and polyoxypropylene derivatives of trimethylolpropane.
(n) Polyhydric alcohol esters, including, but not limited to, ethylene glycol mono- and di-fatty acid esters, diethylene glycol mono- and di-fatty acid esters, polyethylene glycol [M.W. 200–6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.
(o) Wax esters; including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.
(p) Vegetable waxes, including, but not limited to, carnauba and candelilla waxes.
(q) Phospholipids, such as lecithin and derivatives.
(r) Sterols, including, but not limited to, cholesterol and cholesterol fatty acid esters.

(s) Amides, such as fatty acid amides, ceramides, ethoxylated fatty acid amides, and solid fatty acid alkanolamides.

The lotions further preferably contain [by weight] from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g. sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

The balance of the lotion is water or a C2 or C3 alcohol, or a mixture of water and the alcohol. The lotions are formulated by admixing all of the components together. Preferably the inventive compounds are suspended or otherwise uniformly dispersed in the mixture.

In certain embodiments the components may be mixed just prior to use. Devices for effecting such mixture are known to those of skill in the art or are exemplified herein.

(2) Creams

The creams are similarly formulated to contain an effective concentration typically at between about 0.1%, preferably at greater than 1% up to and greater than 50%, preferably between about 3% and 50%, more preferably between about 5% and 15% [by weight] of one ore more the inventive compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included is in the composition at a level from 3% to 50%, preferably from 5% to 20%.

(3) Solutions and Suspensions for Topical Application

These compositions are formulated to contain an amount sufficient to produce a desired effect, for example, moisturising or coloration, typically at a concentration of between about 0.1–10 mg/l preferably between 1 and 5 mg/l of the inventive compounds. The balance is water, a suitable organic solvent or other suitable solvent or buffer. Suitable organic materials useful as the solvent or a part of a solvent system are as follows: propylene glycol, polyethylene glycol [M.W. 200–600], polypropylene glycol [M.W. 425–2025], glycerine, sorbitol esters, 1,2,6-hexanetriol, ethanol, isopropanol, diethyl tartrate, butanediol, and mixtures thereof. Such solvent systems can also contain water.

Solutions or suspensions used for topical application can include any of the following components: a diluent, such as water saline solution, fixed oil, polyethylene glycol, glycerine, propylene glycol or other synthetic solvent; anti-microbial agents, such as benzyl alcohol and methyl parabens; antioxidants, such as ascorbic acid and sodium bisulfite; chelating agents, such as EDTA; buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline [PBS], and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or, may be formulated as an aerosol or foam and applied to the skin as a spray-on. The aerosol compositions typically contain [by weight] from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Solutions, may be formulated as 0.01%–10% isotonic solutions, pH about 4–8, with appropriate salts, and preferably containing one or more of the compounds herein at a concentration of about 0.1%, preferably greater than 1%, up to 50% or more. Suitable mild solutions are known to those of skill in the art. Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium __-hydroxybutyrate and 5–5.5 mM glucose.

The active materials can also be mixed with other active materials, that do not impair the desired action, or with materials that supplement the desired action.

(4) Gels

Gel compositions can be formulated by admixing a suitable thickening agent to the previously described solution or suspension compositions. Examples of suitable thickening agents have been previously described with respect to the lotions.

The gelled compositions contain an effective amount of one or more an anti-hyperalgesic amount, typically at a concentration of between about 0.1 mg/l–10 mg/l or more of one or more of the inventive compounds provided herein, from 0% to 75%, from 0.5% to 20%, preferably from 1% to 10% of the thickening agent; the balance being water or other aqueous carrier.

(5) Solids

Compositions of solid forms may be formulated as stick-type compositions intended for application to the lips or other parts of the body. Such compositions contain an effective amount of one or more of the compounds provided herein. The amount is typically an amount effective to produce the desired result, for example coloration, moisturing and the like when contacted with skin, such as lips, typically at a concentration of between about 0.1 mg/l–10 mg/l or more of one or more of the compounds provided herein. The solids also contain from about 40% to 98%, preferably from about 50% to 90%, of the previously described emollients. This composition can further contain from 1% to 20%, preferably from 5% to 15%, of a suitable thickening agent, and, if desired or needed, emulsifiers and water or buffers. Thickening agents previously described with respect to lotions are suitably employed in the compositions in solid form.

The lipsticks can contain from 0% to about 35%, preferably from about 1% to about 20% and most preferably from about 5% to about 15% of at least one of the inventive compounds.

Flavor oils such as peppermint oil, orange oil, citrus oil, or wintergreen oil can be used along with an alcohol or glycerine. Flavor oils are usually mixed in a solvent such as ethanol to dilute the flavor. The flavor oils useful herein can be derived form natural sources or be synthetically prepared. Generally, flavor oils are mixtures of ketones, alcohols, fatty acids, esters and terpenes. The term "flavor oil" is generally recognized in the art to be a liquid which is derived from botanical sources, i.e. leaves, bark, or skin of fruits or vegetables, and which are usually insoluble in water. The level of flavor oil used can range for 0% to about 5%, preferably from 0% to about 1% of the lipstick composition.

Other ingredients, such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

Pharmaceutical Preparations

The compounds of this invention are administered at a therapeutically effective dosage, i.e., that amount which, when administered to a mammal in need thereof, is sufficient to effect treatment, as described above (for example, to reduce or otherwise treat inflammation, pain and/or pyrexia in the mammal). Administration of the active compounds and salts described herein can be via any of the accepted modes of administration for agents that serve similar utilities.

The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably the drug is present at a level of about 10% w to about 70% w.

Generally, an acceptable daily dose is of about 0.0001 to 150 mg per kilogram body weight of the recipient per day, preferably about 0.01 to 75 mg per kilogram body weight per day, and most preferably about 0.1 to 30 mg per kilogram body weight per day. Thus, for administration to a 70 kg person, the dosage range would be about 0.007 mg to 10.5 g per day, preferably about 0.7 to 5.25 g per day, and most preferably about 7.0 mg to 2.1 g per day.

Administration can be via any accepted systemic or local route, for example, via parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages.

The compositions will include a conventional pharmaceutical carrier or excipient and at least one of the active inventive compounds and, in addition, may include other medicinal agents, pharmaceutical agents, carriers, adjuvants, etc. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical carriers include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with at least one of the inventive compounds. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Intravenous Administration

Intravenous injection has proven to be an important route of administration for antiviral agents. The compounds of the present invention can be administered via this route, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral Administration

Oral administration can be used to deliver the inventive compounds using a convenient daily dosage regimen which can be adjusted according to the degree of affliction or for renal impairment, or to compensate for the toxic effects of other medications administered contemporaneously. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/wt % and 99.99 wt/wt % of the inventive compound, but preferably such compositions will contain between 25 wt/wt % and about 80 wt/wt %.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Liposomal Formulations

Pharmaceutical formulations based on liposomes have recently reached human clinical trials. Their benefits are believed related to favorable changes in tissue distribution and pharmnacokinetic parameters that result from liposome entrapment of drugs, and may be applied to the compounds of the present invention by those skilled in the art.

The formulations can be designed to either target drug to disease sites [see: Lopez-Berestein et al., *J. Infect. Dis.*, 151: 704–710 (1985); Gotfredsen et al., *Biochemical Pharmacology*, 32: 3389–3396 (1983)]; or to the reticuloendothelial system [see Eppstein et al., *Int. J. Immunotherapy*, 2: 115–126 (1986)], to increase duration of drug action [see: Gabizon et al., *Cancer Res.*, 42: 4734 (1982); Eppstein et al., *Delivery Systems for Peptide Drugs*, Eds. S. S. Davis, L. Illum and E. Tomlinson, Plenum Pub. Corp., New York, pp. 277–283; C. A. Hunt, *Biochemica et Biophysica Acta.*, 719: 450–463 (1982); and Senior et al., *Biochemica et Biophysica Acta.*, 839: 1–8 (1985)], or to divert a drug away from organs that are particularly sensitive to its effects [see: Weinstein et al., *Pharmac. Ther.*, 24: 207–233 (1983); Olson et al., *Eur. J. Cancer Clin. Oncol.*, 18: 167–176 (1982); and Gabzion et al., supra.].

Controlled release liposomal liquid pharmaceutical formulations for injection or oral administration are described in U.S. Pat. No. 4,016,100. Liposomal applications for oral drug delivery of a lyophilized liposome/peptide drug mixture filled into intestine capsules have also been suggested, see U.S. Pat. No. 4,348,384. The foregoing is incorporated herein by reference.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/wt % to about 10 wt/wt %; preferably from about 1 wt/wt % to about 2 wt/wt %.

Liquids

Liquid pharmaceutically administrable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Analogs

A mass of 363 mg (Z)-5-[[5-hydroxy-6-methyl-3-[(phosphonooxy)methyl]-4-pyridinyl]methylene]-2-thioxo-4-thiazolidinone (1.0 mmol) was mixed with 20.0 ml of 0.10 M sodium hydroxide solution (2.00 mmol NaOH). After the mixing with 10.0 ml of absolute ethanol the mixture was frozen for 24 h at a temperature of −18° C. The fine crystalline needles were filtered; yield: 340 mg (63%) red (Z)-5-[[3-Hydroxy-2-methyl-5-[(phosphonooxy)methyl]-4-pyridinyl]methylene]-2-thioxo-4-thiazolidinone monosodium salt (8½) hydrate. Before elemental analysis this product was dried for two days at a pressure of 0.1 mbar and a temperature of 70° C.; yield: deep red (Z)-5-[[5-Hydroxy-6-methyl-3-[(phosphonooxy)methyl]-4-pyridinyl]methylene]-2-thioxo-4-thiazolidinone monosodium salt-hemihydrate (2½) hydrate.

8.70 g dry acid (24.00 mmol) were mixed with 240.00 ml of 0.10 M sodium hydroxide solution (24.00 mmol NaOH) and the addition of 124.00 ml of ethanol followed. The mixture was stored 24 h at a temperature of −18° C. The precipitated red crystals were filtered; yield: 7.55 g (73%) of the title compound.

mp 205–208° C. (dec., uncorr.).

Anal. $C_{11}H_{10}N_2NaO_6PS_2 \times 2\frac{1}{2}H_2O$, M=429,33 g/mol; C, 30.77%; H, 3.52; N, 6.52%; found C, 30.97%; H, 3.43%; N, 6.35%. FT IR (KBr): 3277 (vO—H,m, broad), 1700 (vHN—C=O,w), 1229 (vP=O in R—O(HO)PO$_2$,s), 1198 (vHN—C=S,s), 1090 (vC=S, in S—CS—N,s), 973 (vP—O—C in P—O—CH$_2$-aryl,2).

Carminic acid is suspended in dichloromethane and pyridine and 1,3-dicyclohexyl-carbodiimide is added. The mixture is stirred under nitrogen for 60–72 hours and filtered. The filtrate is stirred under nitrogen and a suspension of (Z)-5-[[5-hydroxy-6-methyl-3-[(phosphonooxy)methyl]-4-pyridinyl]methylene]-2-thioxo-4-thiazolidinone in pyridine is added followed by the addition of 4-dimethylaminopyridine. The mixture is stirred for 48–60 hours to isolate the carminic acid conjugate. The resulting pigment exhibits an orange red fluorescence emission at 575 mm.

In an analogous manner and using suitable protecting groups, the pantothenic, β-D-glucuronic and hyaluronic acid polyester conjugates are prepared.

Example 2

Tablet Formulation

This example illustrates the preparation of a representative pharmaceutical formulation containing an active compound of Formula I.

A tablet for oral administration is prepared having the following composition:

| Ingredients | Quantity (mg/tablet) |
|---|---|
| Active compound | 400 mg |
| corn starch | 50 mg |
| lactose | 145 mg |
| magnesium stearate | 5 mg |

The above ingredients are mixed intimately and pressed into single scored tablets.

Other compounds of Formula I can be used as the active compound in the preparation of the tablet formulations of this example.

Example 3

Capsule Formulation

This example illustrates the preparation of a representative pharmaceutical formulation for oral administration containing an active compound of Formula I.

| Ingredients | Quantity (mg/capsule) |
|---|---|
| Active compound | 200 mg |
| lactose, spray-dried | 148 mg |
| magnesium stearate | 2 mg |

The above ingredients are mixed and introduced into a hard-shell gelatin capsule.

Example 4

Oral Formulation

This example illustrates the preparation of a representative pharmaceutical formulation containing an active compound of Formula I.

An suspension for oral administration is prepared having the following composition:

| Ingredients | Quantity |
|---|---|
| Active compound | 1.0 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Other compounds of Formula I can be used as the active compound in the preparation of the orally administrable formulations of this example.

Example 5

| Cream Formulation | |
|---|---|
| Compound of formula (I) | 0.1 g |
| Propylene glycol | 20.0 g |
| Polyethylene glycol 400 | 20.0 g |
| Polysorbate 80 | 1.0 g |
| Water | q.s. 100 mL |

The compound of formula (I) is dissolved in propylene glycol, polyethylene glycol 400 and polysorbate 80. A sufficient quantity of water is then added with stirring to provide 100 mL of the solution which is filtered and bottled.

This example illustrates the preparation of a representative pharmaceutical formulation for parenteral administration containing a compound of formula (I), or a pharmaceutically acceptable salt thereof:

The compound of formula (I) is dissolved in propylene glycol, polyethylene glycol 400 and polysorbate 80. A sufficient quantity of 0.9% saline solution is then added with stirring to provide 100 mL of the I.V. solution which is filtered through a 0.2" membrane filter and packaged under sterile conditions.

Example 6

Suppository Formulation

This example illustrates the preparation of a representative pharmaceutical composition in suppository form containing a compound of formula (I), or a pharmaceutically acceptable salt thereof:

| Ingredients | % wt./wt. |
|---|---|
| Compound of formula (I) | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 7

Nebulized Formulation

This example illustrates the preparation of a representative pharmaceutical formulation in nebulized form containing a compound of formula (I), or a pharmaceutically acceptable salt thereof:

| Ingredients | % wt./wt. |
| --- | --- |
| Compound of formula (I) | 0.005% |
| Water | 89.995% |
| Ethanol | 10.000% |

The compound of formula (I) is dissolved in ethanol and blended with water. The formulation is then packaged in a nebulizer equipped with a dosing pump.

Example 8

Aerosol Formulation

This example illustrates the preparation of a representative pharmaceutical formulation in aerosol form containing a compound of formula (I), or a pharmaceutically acceptable salt thereof:

| Ingredients | % wt./wt. |
| --- | --- |
| Compound of formula (I) | 0.10% |
| Propellant 11/12 | 98.90% |
| Oleic acid | 1.00% |

The compound of formula (I) is dispersed in oleic acid and the propellants. The resulting mixture is then poured into an aerosol container fitted with a metering valve.

Example 9

Lipstick Formulation

This example illustrates the preparation of a representative formulation in lipstick form containing a compound of formula (I), or an acceptable salt thereof:

| Ingredients | % wt./wt. |
| --- | --- |
| Compound of formula (I) | 12.00% |
| diisopropyl dimerate | 12.00% |
| Waxes | 14.50% |
| Oils | 36.50% |
| Gelling Agents | 6.30% |
| Surfactants/Emulsifiers | 12.65% |
| Polar Solvent | 6.00% |
| Preservatives | 0.05% |

The pigment is slurried in the diisopropyl dimerate. Add and mix into the slurry the oils and the thickening/gelling agent (hydrophobic clay and activator). The mixture is heated to about 85 degree C. with stirring. The surfactants and polar solvents are mixed together to form the surfactant association structure phase. The surfactant association structure mixture and the remaining ingredients are added to the thickening/gelling agent mixture with constant stirring until a homogeneous mixture is achieved. Once uniform, the composition is poured into molds at room temperature.

Example 10

Lotion Formulation

This example illustrates the preparation of a representative lotion formulation containing a compound of formula (I), or an acceptable salt thereof:

| | Ingredients | % wt./wt. |
| --- | --- | --- |
| (1) | Compound of formula (I) | 1.00% |
| (2) | diglyceryl monooleate | 4.00% |
| (3) | aluminum tristearate | 0.08% |
| (4) | liquid paraffin | 8.00% |
| (5) | isopropyl myristate | 2.00% |
| (6) | potassium suifate | 1.00% |
| (7) | methylparaben | 0.20% |
| (8) | 1,3-butylene glycol | 2.00% |
| (9) | purified water | balance |
| | in total | 100.00 |

The components (2) to (5) are melted by heating to 70 degree C. to thereby give an oily phase. Separately, the components (6) to (9) are dissolved by heating to 70 degree C. to thereby give an aqueous phase. Then the aqueous phase is added to the oily phase and the obtained mixture is emulsified by stirring. Next, the component (1) is added thereto and dispersed therein by stirring. The mixture is cooled to room temperature under further stirring. Thus, a cream preparation containing at least one inventive compound is obtained. The lotion may also contain propyl paraben as well as disodium EDTA as preservatives, color and fragrance, if so desired.

Example 11

Insufflation Formulation

This example illustrates the preparation of a representative pharmaceutical formulation for insufflation containing a compound of formula (1), or a pharmaceutically acceptable salt thereof:

| Ingredients | % wt./wt. |
| --- | --- |
| Micronized compound of formula (I) | 1.0% |
| Micronized lactose | 99.0% |

The ingredients are milled, mixed, and packaged in an insufflator equipped with a dosing pump.

Example 12

Nail Lacquer Formulation

The general formulation for UV-curable fingernail polishes containing modified cellulose esters of the present invention is as follows:

| Ingredients | % wt./wt. |
| --- | --- |
| modified cellulose ester as the major film former | 5–50% |
| copolymerizable monomer | 10–90% |
| modifying resin | 0–10% |
| plasticizer | 0–25% |
| pigment, including compounds of Formula I | 0–5% |
| photoinitiator | 2–7% |
| solvents | 0–90% |

Example 13

Treatment of a Rhinovirus Infection

A 25 year old male patient with a common katarrhalic infection (common cold) was treated orally with 50 mg of (2RS,4R)-2-[3-Hydroxy-5-(hydroxymethyl)-2-methyl-4-pyridinyl]-4-thiazolidine carboxylic acid in a water solution. After 15 minutes the disease symptoms disappeared.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not limiting. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:
1. A compound having the formula:

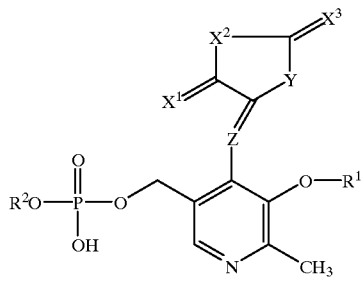

wherein
  $R^1$ is hydrogen, or acyl with 2–22 carbons (excluding retinoyl);
  $R^2$ is hydrogen, or aryl with 6–30 carbons; provided that at least one of $R^1$ or $R^2$ is not hydrogen;
  $X^1$, $X^2$ and $X^3$ are independently O, S, or $NR^3$;
  $R^3$ is hydrogen, alkyl with 1–6 carbons, or acyl with 2–6 carbons;
  Y is O, S, or NH;
  Z is CH or N;
  or salts or esters derived therefrom.

2. A compound having the structure:

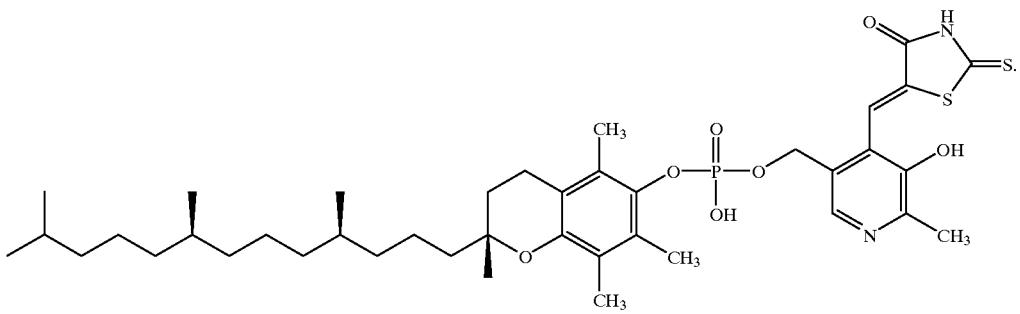

3. A compound having the structure:

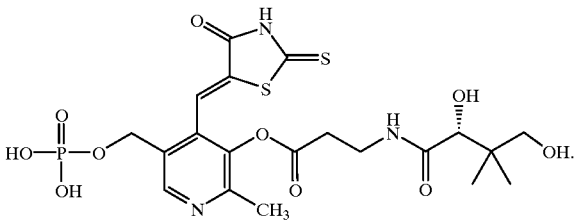

4. A compound having the structure:

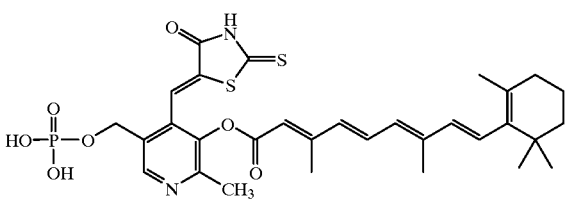

5. A compound having the structure:

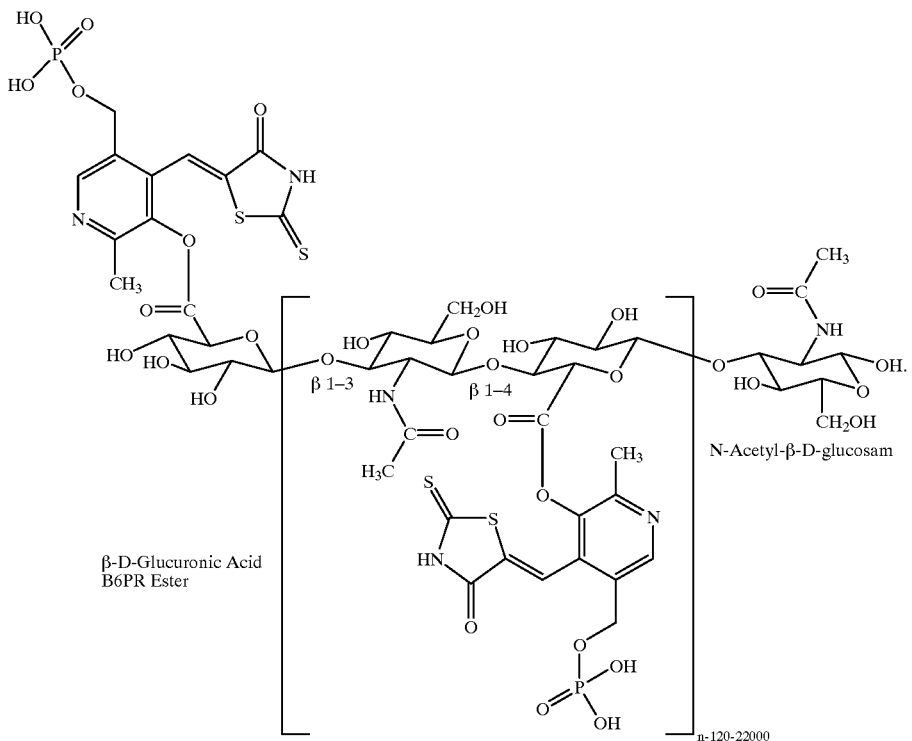

6. A compound having the structure:

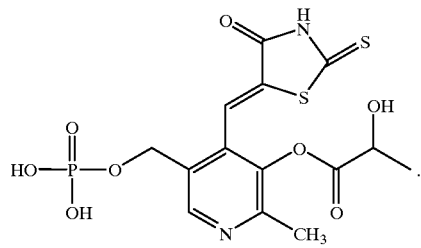

7. A pharmaceutical composition comprising a pharmaceutically acceptable excipient and a therapeutically effective amount of a compound of claim 1.

8. A skin care composition comprising a cosmetically acceptable carrier and an effective amount of a compound of claim 1.

9. A method of regulating a skin condition, which method comprises applying to the skin of a mammal a safe and effective amount of the compound according to claim 1.

* * * * *